United States Patent [19]

Zucker

[11] Patent Number: 5,662,121
[45] Date of Patent: Sep. 2, 1997

[54] MEDICAL DIAGNOSTIC DEVICE FOR APPLYING CONTROLLED STRESS TO JOINTS

[76] Inventor: Ivan Zucker, 1703 Chippewa Ridge, Ambler, Pa. 19002

[21] Appl. No.: 410,023

[22] Filed: Mar. 14, 1995

[51] Int. Cl.⁶ ................................................. A61B 5/103
[52] U.S. Cl. ................................................. 128/774
[58] Field of Search .............................. 128/774, 782, 128/779; 602/16, 20, 23, 33, 26

[56] References Cited

U.S. PATENT DOCUMENTS

| | | | |
|---|---|---|---|
| 4,534,364 | 8/1985 | Lamoreux | 128/774 |
| 4,909,262 | 3/1990 | Halpern et al. | 128/774 |
| 5,251,629 | 10/1993 | Koizumi et al. | 128/653.2 |
| 5,263,492 | 11/1993 | Voyce | 128/782 |
| 5,403,350 | 4/1995 | McAtee | 606/241 |

OTHER PUBLICATIONS

Tung, "Tears of the Anterior Cruciate Ligament: Primary and Secondary Signs at MR Imaging", Radiology 1993; 188:661–667.
Koybayashi, "Quantitative Stress Radiography for Diagnosis of Anterior Cruciate Ligament Deficiency", Archives of Orthopaedic Trauma Surgery (1993) 112:109–112.
Kärrholm "Chronic Anterolateral Instability of the Knee a Roentgen Sterophotogrammetric Evaluation", The American Journal of Sports Medicine, vol. 17, No. 4, 1989, pp. 555–563 (Jul. 1989).
Fukubayshi, "An in Vitro Biomechanical Evaluation of Anterior-Posterior Motion of the Knee", The Journal of Bone and Joint Surgery vol. 64–A, No. 2 (Feb. 1982) pp. 258–264.
Shellock, "Patellofemoral Joint: Identification of Abnormalities with Active-Movement, 'Unloaded' versus 'Loaded' Kinematic MR Imaging Techniques", Radiology 1993; 188:575–578.
Stenlund, "Diminished Space in the Acromioclavicular Joint in Forced Arm Adduction as a Radiographic Sign of Degeneration and Osteoarthrosis", Skeletal Radiology (1992) 21:529–533.
Schiund, "The Distal Radioulnar Ligaments:", The Journal of Hand Surgery, vol. 16A, No. 6. pp. 1106–1114 (Nov. 1991).
Savelberg, "Strains and Forces in Selected Carpal Ligaments During In Vitro Flexion and Deviation Movement of the Hand", Journal of Orthopaedic Research, vol. 10, No. 6. pp. 901–910 (Nov. 1992).
Vahey, "Anterior Translocation of the Tibia at MR imaging:", Radiology 1993; 187:817–819.

Primary Examiner—Max Hindenburg
Assistant Examiner—Pamela L. Wingood
Attorney, Agent, or Firm—Seidel Gonda Lavorgna & Monaco, P.C.

[57] ABSTRACT

A medical diagnostic device for applying a desired stress to a limb joint has a frame, a limb-restraint at a first end of the frame for immobilizing a first limb portion on one side of the joint, a cradle at a second end of the frame for receiving and supporting a second limb portion on the opposite side of the joint, a reciprocable member connected between the frame and cradle and constrained to move a preselected distance between a first position in which the cradle is proximal to the frame and a second position in which the cradle is remote from the frame, and a driver for controllably moving the reciprocable member from the first position to the second position. Movement of the reciprocable member moves the cradle from a position in which the joint is relaxed to a position in which the joint is subjected to the controlled stress. The invention also covers a method of applying a desired stress to a limb joint, comprising the steps of immobilizing a first limb portion on one side of the joint, receiving a second limb portion on the opposite side of the joint in a movable cradle, and applying a preselected force on the second limb portion by moving the cradle by a preselected amount from a first position in which the joint is relaxed to a second position in which the joint is subjected to the desired stress.

18 Claims, 4 Drawing Sheets

1

MEDICAL DIAGNOSTIC DEVICE FOR APPLYING CONTROLLED STRESS TO JOINTS

FIELD OF THE INVENTION

The present invention relates to medical diagnostic devices for applying controlled stress to joints to permit more accurate diagnosis and imaging of human joints, such as but not limited to the knee. While for convenience the present invention will be described in the context of diagnosing knee injuries, such as ligamentous injuries, it should be understood that the invention is not limited to any particular joint or any particular injury to a joint. The invention has wide utility in diagnosing all types of joint injuries and pathologies.

BACKGROUND OF THE INVENTION

Injuries to joints are a common medical problem, but due to the complexity of most joints it is often difficult to make accurate diagnoses. This is especially true of the knee. One common injury to a joint is injury to the anterior cruciate ligament (ACL) of the knee. This type of injury, while common, is not always easy to diagnose. In deference to the patient, physicians prefer not to perform surgery on the knee, or indeed on any other joint, in order to exclude a diagnosis. Thus, it is desired to use non-invasive techniques.

One non-invasive way of diagnosing injuries to the ACL is to elicit anterior translocation of the tibia. Anterior translocation of the tibia is an indirect way of diagnosing ACL tears. It is known that, in a healthy knee, the tibia can move (translocate) anteriorly relative to the femur by about 4 mm when an anteriorly-directed force of about 100 N (approximately 25 pounds) is applied to the tibia. Excessive anterior translocation of the tibia under such a force is a direct indication of ligamentous instability in the knee, usually but not always as a result of tears in the ACL. By manually applying an anteriorly-directed force on the tibia, such as by pulling anteriorly on the leg while holding the thigh still, a physician can feel instability in the knee due to ACL injury. (As used herein, the term "leg" refers to that portion of the lower limb below the knee, and the term "thigh" refers to that portion of the limb above the knee.) However, as might be expected, this method is imprecise in that the amount of force manually applied, and the resulting translocation of the tibia, cannot be quantitatively measured. Moreover, uncommonly individuals with healthy knees will exhibit anterior translocation greater than 4 mm, while some injured knees may exhibit only 4 mm or less anterior translocation. This can result in invasive testing on patients without ACL tear. Thus, while the hands of a skilled physician can help make a diagnosis, a quantitatively more precise way of diagnosing ACL injuries, as well as other possible etiologies, is desired.

Magnetic resonance imaging and arthroscopy are two ways of obtaining more accurate diagnoses of joint injuries. Magnetic resonance imaging (MRI) is non-invasive and, although arthroscopy is technically invasive, it is far less insulting to the joint than surgery. MRI and arthroscopic probes thus have enabled physicians to see into a joint without surgery. These techniques have enabled better diagnoses and have reduced unnecessary surgery, but even such techniques have their limits. For example, tears in the anterior cruciate ligament are particularly problematic because it is virtually impossible to get good visualization of the proximal ACL with an arthroscope and sometimes difficult with MRI. The ACL often tears behind the femoral condyles, and it is difficult to insert an arthroscope behind the condyles to view the ACL. Magnetic resonance imaging can "see" behind the condyles, but often lacks sufficient resolution to image the fine detail needed to determine the existence of a tear because MRI is subject to volume averaging artifacts. That is, there is a limit to the resolution available h MRI due to the size of the "voxels," or volume elements, into which the object (in this case the ACL and femoral condyles) being imaged can be divided by the MRI processor. Because of the difficulty in making an accurate diagnosis using arthroscopy and conventional MRI, unnecessary arthroscopy, or even surgery, may be performed, or necessary surgery may be deferred.

MRI examination is also often adversely affected by the physical constraints imposed by the MRI equipment. In order to image a knee, for example, the knee must be placed inside the MRI magnetic coil. The position into which the patient's leg is put can be variable with current technology, and it is sometimes difficult for the patient to keep the leg in the required position during imaging. In addition, in many cases only the patient's thigh is supported, and the weight of the patient's leg and foot levering against the coil housing tend to cause the knee to bend or the tibia to translocate anteriorly. This puts an unknown and unwanted stress on the joint, and consequently the physician can not be certain whether the resulting MRI image shows an injury or merely an effect of an unquantifiable stress on an otherwise healthy knee. On the other hand, it may only variably reveal true ACL injuries, thereby decreasing diagnostic accuracy.

Accordingly, there is a need for a way of diagnosing joint injuries that does not rely solely on manual evaluation, which does not place unwanted and unquantifiable stresses on the joint, and which is not subject to the current limitations on arthroscopic and conventional MRI procedures. There is also a need for a way of diagnosing joint injuries which is compatible with, and complements, conventional MRI procedures. The present invention fills those needs.

SUMMARY OF THE INVENTION

The present invention is directed to a medical diagnostic device for applying a desired stress to a limb joint. The device comprises a frame, a limb-restraint at a first end of the frame for immobilizing a first limb portion on one side of the joint, a cradle at a second end of the frame for receiving and supporting a second limb portion on the opposite side of the joint, a reciprocable member connected between the frame and the cradle and constrained to move between a first position in which the cradle is proximal to the frame and a second position in which the cradle is remote from the frame, and a driver for controllably moving the reciprocable member from the first position to the second position. Movement of the reciprocable member moves the cradle from a position in which the joint is relaxed to a second position in which the joint is subjected to the controlled stress.

The invention also covers a method of applying a desired stress to a limb joint, comprising the steps of immobilizing a first limb portion on one side of the joint, receiving a second limb portion on the opposite side of the joint in a movable cradle, and applying a preselected force on the second limb portion by moving the cradle from a first position in which the joint is relaxed to a second position in which the joint is subjected to the desired stress.

DESCRIPTION OF THE DRAWINGS

For the purpose of illustrating the invention, there is shown in the drawings a form which is presently preferred.

it being understood, however, that this invention is not limited to the precise arrangements and instrumentalities shown.

DESCRIPTION OF THE INVENTION

Figure 1:
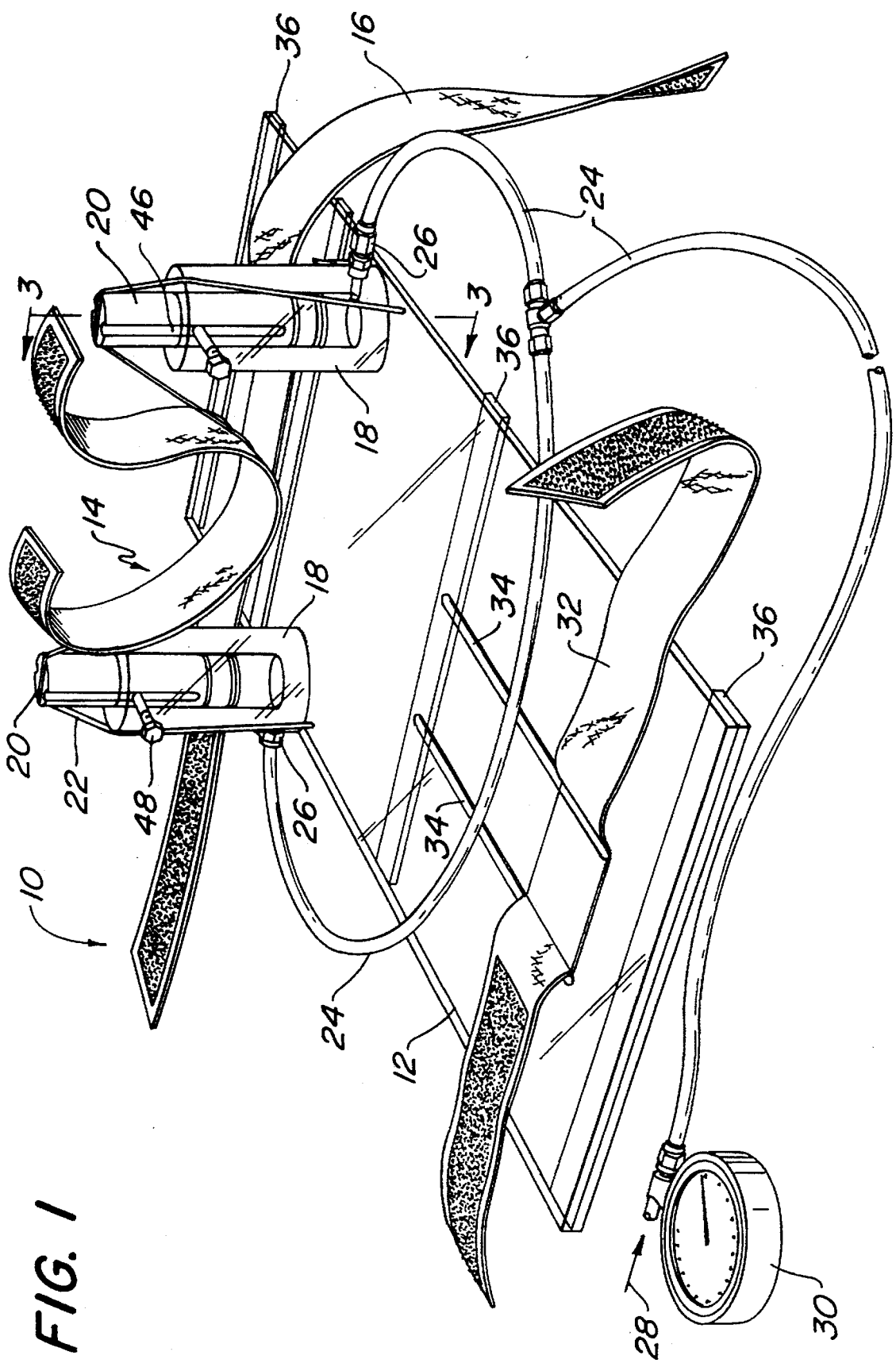
FIG. 1 is an isometric view of a diagnostic device according to the present invention.

Referring now to the drawings, wherein like numerals indicate like elements, there is shown in FIG. 1 a device 10 in accordance with the present invention. The device 10 comprises a frame 12, a cradle 14, and a first restraint 16. Frame 12 is generally rectangular, and is flat, or planar, and has an upper surface and a lower surface. A pair of cylinders 18 are mounted on the upper surface of frame 12. Both cylinders are the same, so only one need be described in detail. Cylinder 18 includes a piston 20 which is mounted for reciprocable movement within the cylinder. Cradle 14 is connected to pistons 20 by a cord 22, which runs between the two pistons. Cord 22 and its connections and functions will be described in greater detail below.

Cylinders 18 are pressurized by a source of pressurized fluid, such as air, via hoses 24 and firings 26. Pressurized fluid, represented by the arrow labelled 28 in FIG. 1, is supplied from a source of pressurized fluid (not shown) in conventional manner. A gauge 30 is included to provide an indication of the pressure of the fluid being supplied to the cylinders 18.

Frame 12 may also be provided with a second restraint 32, on the opposite side of the cylinders from restraint 16. Restraint 32 is, however, optional, and is not crucial to the invention. Restraints 16 and 32 are illustrated as elongated straps, which include hook-and-loop fasteners to cinch the straps in place. However, while the preferred embodiment is illustrated, it should be understood that the restraints 16 and 32 may have any suitable form. In the preferred embodiment, where the restraints 16 and 32 are in the form of elongated straps, longitudinal slots such as slots 34 are provided in frame 12. Slots 34 permit the straps to be secured to the frame, while permitting their position to be adjusted to accommodate limbs of different size.

Frame 12 may further include feet 36 on the lower surface to support frame 12 and to leave a small space between frame 12 and a surface on which frame 12 is placed.

Figure 2:
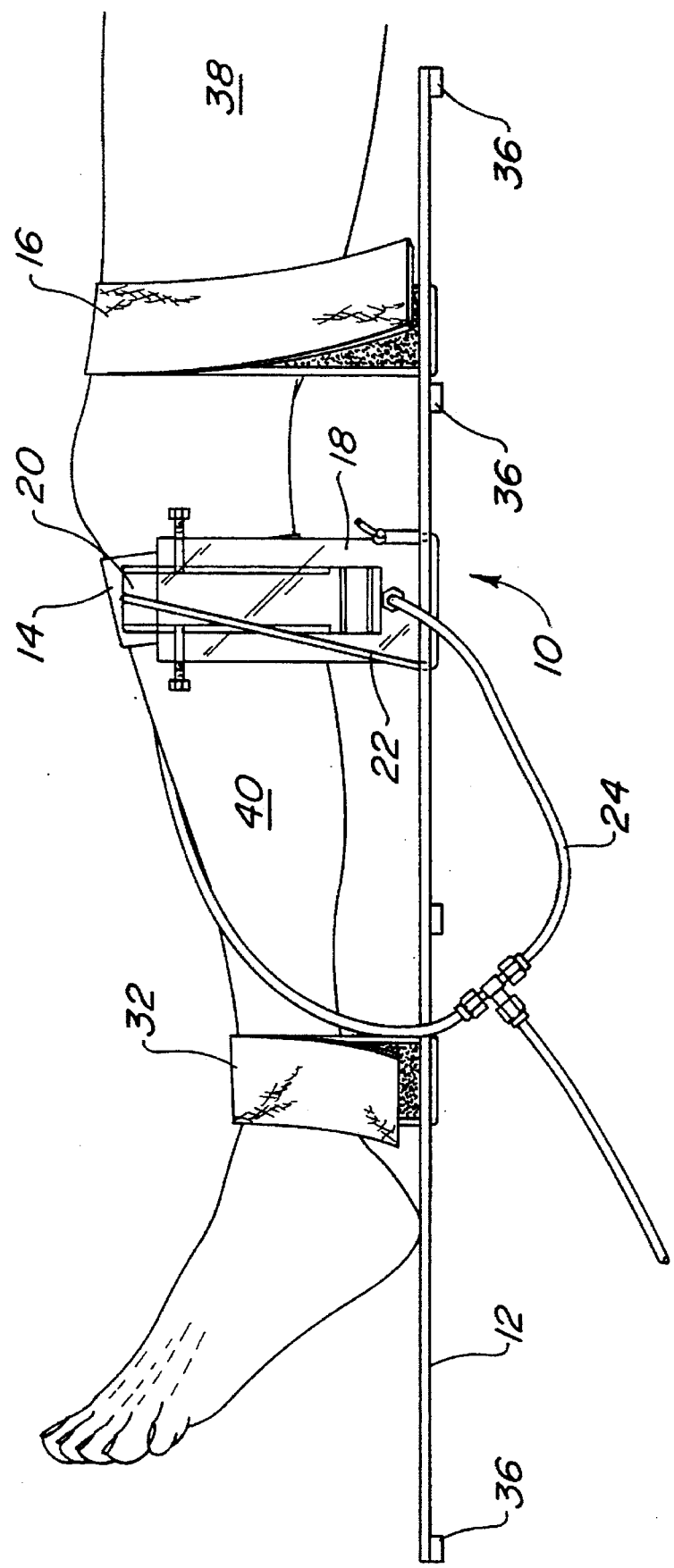
FIG. 2 is a side elevational view of the apparatus of FIG. 1, showing how the apparatus is used in conjunction with a leg.

FIG. 2 illustrates the manner in which the invention is used in order to apply a controlled stress to a knee in order to perform anterior translocation of the tibia, for example. By placing a controlled stress on the knee, ligamentous injury such as tears in the ACL may be more readily observed in MRI testing. A patient's lower limb is placed on the frame 12 with the thigh 38 at one end of the frame and the leg 40 at the other. Thigh 38 is restrained from moving by restraint 16. Leg 40 is received in and supported by cradle 14. Restraint 32 may be used to restrain the patient's ankle, although that is not absolutely necessary. In FIG. 2, the cylinders are illustrated in an unpressurized state, and hence no external force is being applied to the patient's leg by cradle 14. When the cylinders are pressurized, however, cradle 14 is moved from the position shown in FIG. 2, where the cradle 14 is proximal to frame 12, to a position where cradle 14 is more remote from frame 12.

Figure 3:
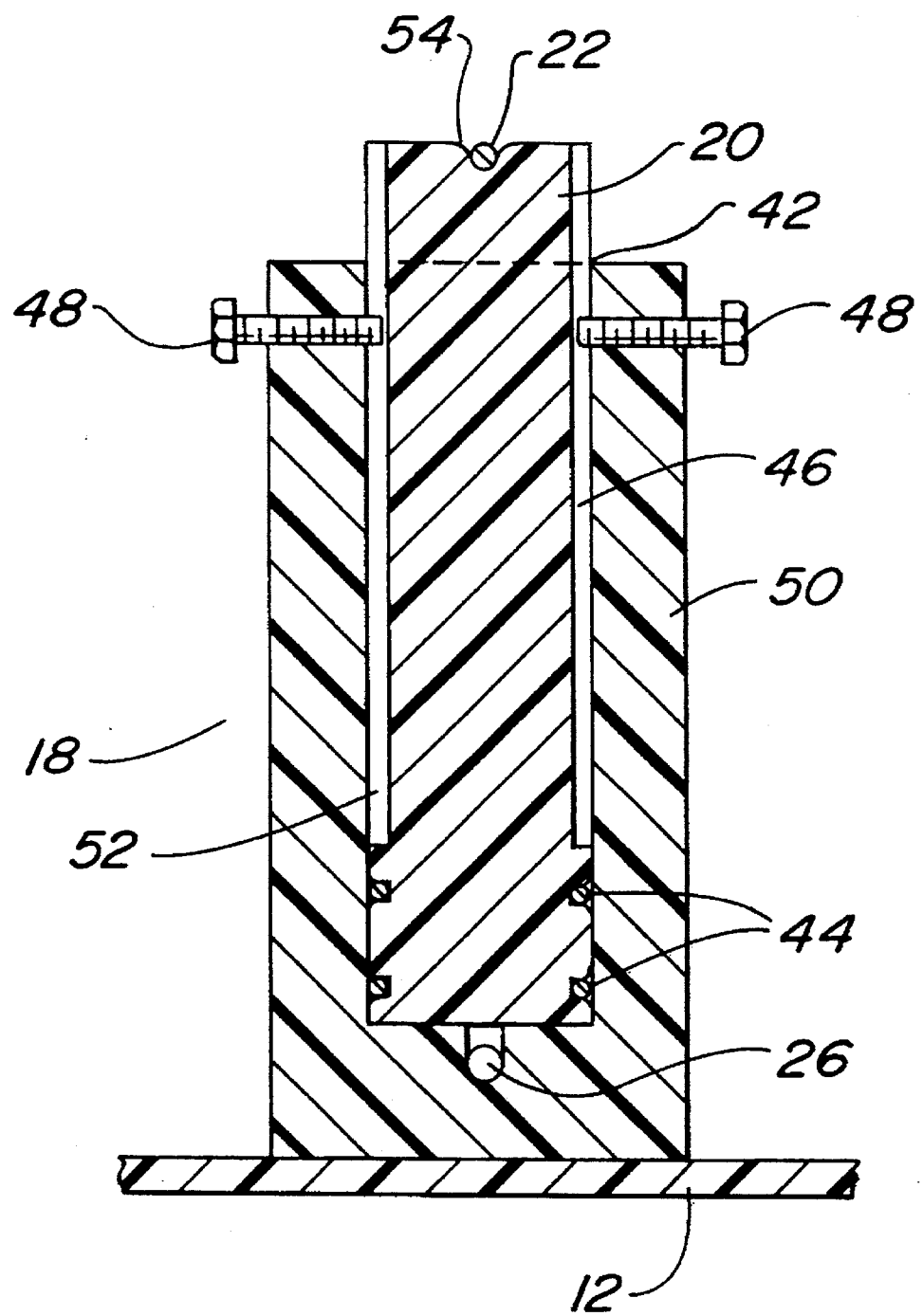
FIG. 3 is a sectional view taken along the lines 3—3 in FIG. 1.

How cylinders 18 operate to move cradle 14 is best understood by reference to FIG. 3, which is a cross-sectional view of one of the cylinders. Cylinder 18 has an internal bore 42 in which piston 20 moves. The diameter of the bore and the diameter of the piston are chosen so that the piston 20 fits snugly within bore 42, but is still free to move without binding. As already noted, pressurized fluid is introduced into cylinder bore 42 via fitting 26. The pressurized fluid tends to force piston 20 to move upward. Seals 44 are provided around the circumference of piston 20 to minimize leakage of the pressurized fluid between the piston and the bore. As best seen in FIGS. 1 and 3, piston 20 is provided with at least one, and preferably two, grooves or channels 46, which begin at the top end of piston 20 and terminate just short of the bottom end of the piston. The length of the grooves determines the maximum upward travel of the piston 20 when the cylinder is pressurized. Grooves 46 cooperate with stops 48 provided at the top end of cylinder 18 to limit the upward movement of piston 20. Stops 48 extend through cylinder wall 50 and a short distance into bore 42. Stops 48 are aligned with grooves 46, and permit unrestricted upward movement of piston 20 until the bottom ends 52 of grooves 46 contact stops 48. Stops 48 are designed to ensure that under no circumstances can pistons 20 be ejected from cylinders 18 when the cylinders are pressurized, in order to avoid potential injury to a patient or damage to equipment.

It will also be understood that upward movement of the pistons will put tension on cord 22, which in turn will raise the cradle 14 away from frame 12, as will now be described. As best seen in FIGS. 1 and 2, cradle 14 is in the form of a sling or elongated strap which is attached to and supported by cord 22. Cradle 14 may be attached to cord 22 in any suitable manner. Cord 22, in turn, is attached at each end to frame 12, such as by slipping the ends through holes in frame 12 and knotting or otherwise fixing the ends to the frame. Cord 22 is then passed over the top ends of pistons 20 in cylinders 18. Cylinders 18 may be provided with a groove 54 (see FIG. 3) across the top to receive cord 22. Alternatively, cylinders 18 may be provided with a transverse bore through the top end, through which cord 22 may be threaded but not secured. It is important that the cord 22 not be secured to pistons 20, so that movement of pistons 20 is not restricted by cord 22, and so that upward movement of pistons 20 will apply tension to cord 22.

When cylinders 18 are pressurized, pistons 20 will move upward until prevented from further upward movement by the opposed force of the weight of the patient's leg. As the pistons 20 move upward, they apply tension to cord 22, which, because the ends of cord 22 are fixed to frame 12, pulls upward on cradle 14. Thus, as the pistons move upward, they raise cradle 14 away from frame 12. When the pressure to cylinders 18 is removed, the weight of the patient's leg on cradle 14 is transmitted through cord 22 to pistons 20, and forces pistons 20 to move downward. The position of cradle with respect to the frame may thus be controlled by the pressure in the cylinder. Preferably, when pressurized, the cylinders are pressurized to a degree that equilibrium is reached between the pressure in the cylinders and the downward force of the weight of the patient's leg. When the cylinders are depressurized, they are completely depressurized, so that the pistons reach their maximum downward movement under the weight of the patient's leg.

Figure 4:
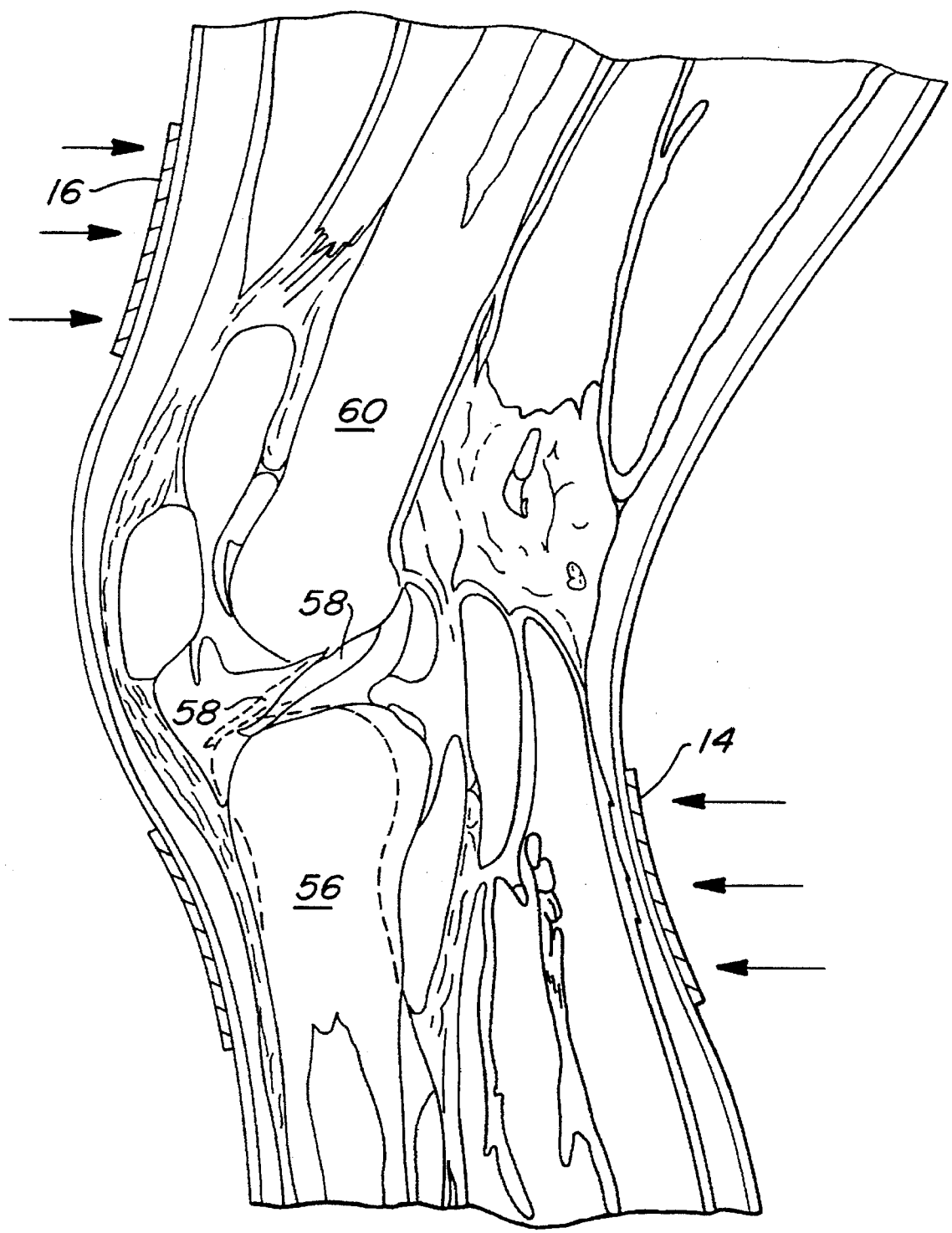
FIG. 4 is a sectional view through a knee, showing movement of the tibia as a result of an applied force on the leg.

The upward movement of cradle 14 applies an anteriorly directed force on the patient's tibia, as best seen in FIG. 4.

In FIG. 4, the tibia 56 is shown in solid lines as it would be without the application of the anteriorly directed force from cradle 14, and is shown in dashed lines in the position in which it would be as a result of the force applied to the patient's leg by cradle 14 when the pistons are pressurized and the cradle 14 is in the equilibrium position. The application of the anteriorly directed force urges the tibia 56 to move anteriorly relative to the femur 60. Anterior movement of the tibia tends to stretch or, if torn, separate the anterior cruciate ligament 58, which is shown in FIG. 4 in its relaxed state in solid lines, and in its stretched state in dashed lines. The amount of movement of the tibia 56 relative to the femur 60 provides an indication of the condition of the ligaments, particularly the ACL, of the knee, and is referred to as "the anterior draw sign." In particular, stretching the ACL makes it easier to observe small tears using MRI.

It will be appreciated that, while the invention is described in the context of diagnosing ligamentous injuries of the knee, the device of the present invention is applicable to diagnosing injuries in other joints, such as the elbow or wrist. It will also be appreciated that the device of the invention is also useful in checking for posterior drawer sign, where the force is applied to the thigh to cause the femur to move relative to the tibia, while the tibia is restrained.

To use the device of the invention to diagnose ligamentous knee injuries, the patient's lower limb is placed in the device 10 as shown in FIG. 2, and the patient's limb and the device 10 are placed adjacent MRI coils (omitted from the drawings for the sake of clarity) for MRI imaging. The cylinders 18 are then pressurized to move cradle 14 away from frame 12, thereby placing the desired anteriorly directed force on the patients tibia.

Since the device 10 is intended to be used with MRI apparatus, it is important that the material from which frame 14 is constructed be nonresponsive to MRI testing (i.e., must not show up on an MRI image). A preferred material is a plastic, such as polycarbonate, but other materials are acceptable provided their proton density is negligible so that they do not interfere with the imaging process. Likewise, since water images strongly on MRI, it is important to avoid the use of hydraulic fluids to pressurize the cylinders 18. The preferred pressurized fluid for pressurizing the cylinders is air, which is readily available and does not appear on MRI images, but other gases can be used if desired.

It will be appreciated that the present invention provides an effective way of applying a controlled stress to a limb joint for diagnostic testing of the joint. Those skilled in the art will recognize from the foregoing disclosure that changes may readily be made to the invention to adapt it for different diagnostic techniques without departing from the scope of the invention. For example, the invention can readily be used with equipment for making X-ray images of a joint when desired. Likewise, those skilled in the art will understand that it is possible to determine the amount of stress placed on a joint by varying the pressure in cylinders 18. Numerous adaptations and modifications to the invention may thus be made, which nevertheless fall within the scope of the present invention.

Since the present invention may be embodied in other specific forms without departing from the spirit or essential attributes thereof, reference accordingly should be made to the appended claims, rather than to the foregoing specification, as indicating the scope of the invention.

I claim:

1. A medical diagnostic device for applying a desired stress to a knee joint of a patient, comprising a frame, a restraint at a first end of the frame for immobilizing the patient's thigh, a cradle at a second end of the frame for receiving and supporting the patient's leg, a pair of reciprocable pistons between the frame and the cradle for supporting the cradle, the pistons being constrained to move within respective cylinders a distance between a first position in which the cradle is proximal to the frame and a second position in which the cradle is remote from the frame, and a source of pressurized fluid connected to the cylinders for controllably moving the pistons from the first position to the second position, the second position being a position of equilibrium between the weight of the patient's leg and a force generated by pressure in the cylinders.

2. A medical diagnostic device according to claim 1, wherein the frame, cradle, pistons and cylinders are made of a material not responsive to magnetic resonance imaging.

3. A medical diagnostic device according to claim 1, wherein the pressurized fluid is a gas.

4. A medical diagnostic device for applying a desired stress to a knee joint of a patient to aid in diagnosis of ligamentous instability in the knee, comprising a frame made of a material not responsive to diagnostic imaging methods, a restraint at a first end of the frame for immobilizing the patient's thigh, a cradle at a second end of the frame for receiving and supporting the patient's leg, a pair of reciprocable pistons between the frame and the cradle for supporting the cradle, the pistons being constrained to move within respective cylinders mounted on said frame a distance between a first position in which the cradle is proximal to the frame and a second position in which the cradle is remote from the frame, movement of the cradle resulting in the application of an anteriorly directed force on the patient's leg, and a source of pressurized air connected to the cylinders for controllably moving the pistons from the first position to the second position, the second position being a position of equilibrium between the weight of the patient's leg and a force generated by pressure in the cylinders, whereby the desired stress is applied to the knee joint when the pistons are in the second position.

5. A medical diagnostic device for applying a desired stress to a joint of a limb comprising:

a support frame, a limb restraint at one end of the frame for immobilizing a first limb portion on one side of the joint, a cradle located near the limb restraint for receiving and supporting a second limb portion on the opposite side of the joint, at least one driver attached to the support frame and engageable with the cradle, the driver being movable between a first position in which the cradle is proximal to the support frame and the joint is relaxed and a second position in which the cradle is remote from the support frame whereby the first limb portion is translocated relative to the second limb portion.

6. The medical diagnostic device according to claim 5, wherein the at least one driver comprises a cylinder and a reciprocable piston movable therein, one of said piston or cylinder being attached to the support frame, the other of said piston or cylinder being engageable with the cradle.

7. The medical diagnostic device according to claim 6, wherein the cradle comprises a cord, the at least one driver applying tension to the cord as the at least one driver moves from the first to the second position.

8. The medical diagnostic device according to claim 7, wherein the at least one driver comprises a pair of drivers located at each end of the cradle.

9. The medical diagnostic device according to claim 8, wherein the support frame, cradle, drivers are made of a material which is not responsive to magnetic resonance imaging.

10. A method of conducting magnetic resonance imaging of ACL injuries in a patient's knee comprising the steps of:

anteriorly translocating the patient's tibia relative to the patient's femur causing the patient's ACL to stretch or separate;

maintaining the patient's ACL in a stretched or separated condition; and taking an MRI scan of the ACL while maintained in the stretched or separated condition.

11. The method of claim 10, wherein the translocating step comprises:

immobilizing the patient's leg above the knee;

receiving the portion of the patient's leg below the knee in a movable cradle; and applying a preselected force on the patient's leg below the knee by moving the cradle from a first position in which the knee is relaxed to a second position in which the patient's tibia is translocated relative to the femur.

12. The method of claim 11, wherein the force applying step comprises:

providing a pair of reciprocable drivers for supporting the cradle;

moving the drivers from a first position in which the cradle is in a relaxed first position to a second position in which the cradle is in the tension second position thereby translocating the patient's tibia relative to the femur.

13. The method of claim 12, wherein the maintaining step comprises maintaining the drivers in the second position thereby maintaining tension on the cradle which maintains the patient's ACL in a stretched or separated condition.

14. A method of conducting magnetic resonance imaging of ligament injuries in a patient's limb joint comprising the steps of:

anteriorly translocating a first limb portion on one side of the joint relative to a second limb portion on the opposite side of the joint causing a ligament of the joint to stretch or separate;

maintaining the ligament in a stretched or separated condition; and taking an MRI scan of the ligament while maintained in the stretched or separated condition.

15. The method of claim 14 wherein the translocating step comprises:

immobilizing the first limb portion;

receiving the second limb portion in a movable cradle; and applying a preselected force to the second limb portion by moving the cradle from a first position in which the limb joint is relaxed to a second position in which the first limb portion is translocated relative to the second limb portion.

16. The method of claim 15 wherein the force applying step comprises:

providing a pair of reciprocable drivers for supporting the cradle;

moving the drivers from a first position in which the cradle is in a relaxed first position to a second position in which the cradle is in the tension second position thereby translocating the first limb portion relative to the second limb portion.

17. The method of claim 16 wherein the maintaining step comprises maintaining the drivers in the second position thereby maintaining tension on the cradle which maintains the ligament in a stretched or separated condition.

18. A method of conducting magnetic resonance imaging of ligament injuries in a patient's limb joint comprising the steps of:

placing a first limb portion on one side of the joint in restraint;

placing a second limb portion on the opposite side of the joint in a movable cradle;

moving the cradle to anteriorly translocate the second limb portion relative to the first limb portion causing a ligament of the joint to stretch or separate;

taking an MRI scan of the ligament while it is maintained in the stretched or separated condition.

* * * * *